United States Patent
Chowdhury et al.

(10) Patent No.: US 10,214,432 B2
(45) Date of Patent: Feb. 26, 2019

(54) METHOD AND DEVICE FOR ONLINE MONITORING OF WATER QUALITY

(71) Applicant: AQUA-Q AB, Farsta (SE)

(72) Inventors: Sudhir Chowdhury, Farsta (SE); Ulla Chowdhury, Farsta (SE)

(73) Assignee: AQUA-Q AB, Farsta (SE)

( * ) Notice: Subject to any disclaimer, the term of this patent is extended or adjusted under 35 U.S.C. 154(b) by 231 days.

(21) Appl. No.: 15/114,536

(22) PCT Filed: Feb. 2, 2015

(86) PCT No.: PCT/SE2015/050113
§ 371 (c)(1),
(2) Date: Jul. 27, 2016

(87) PCT Pub. No.: WO2015/115995
PCT Pub. Date: Aug. 6, 2015

(65) Prior Publication Data
US 2016/0340204 A1  Nov. 24, 2016

(30) Foreign Application Priority Data
Feb. 3, 2014 (SE) .................................... 1450114

(51) Int. Cl.
*C02F 1/44* (2006.01)
*C02F 1/78* (2006.01)
(Continued)

(52) U.S. Cl.
CPC .............. *C02F 1/008* (2013.01); *C02F 1/444* (2013.01); *C02F 1/78* (2013.01); *G01N 1/2035* (2013.01);
(Continued)

(58) Field of Classification Search
CPC .. C02F 1/008; C02F 1/444; C02F 1/78; C02F 2209/008; C02F 2303/04; C02F 2209/06;
(Continued)

(56) References Cited

U.S. PATENT DOCUMENTS 5,798,699 A * 8/1998 Bryant ................. G01N 21/534
250/338.1
2005/0009192 A1  1/2005 Page
(Continued)

FOREIGN PATENT DOCUMENTS

CN      1673717      9/2005
WO      02/17975     3/2002
(Continued)

OTHER PUBLICATIONS

International Search Report dated May 5, 2015 in International (PCT) Application No. PCT/SE2015/050113.
(Continued)

*Primary Examiner* — Joseph W Drodge
(74) *Attorney, Agent, or Firm* — Wenderoth, Lind & Ponack, L.L.P.

(57) ABSTRACT

A method for monitoring quality of a water flow in a pipe, by diverting a flow into a laser particle counter to count particles within a particle size interval in the water, to continuously determine the number of particles within the size interval, comparing the count with a reference value and taking a sample of the water from the pipe when the count exceeds a threshold value, and also diverting a flow of water from the pipe into a unit that separates the flow into fractions, and taking a sample of at least one of said fractions when the count exceeds a threshold value, and also sending an alarm signal when the count exceeds a threshold value. When the count exceeds at threshold value, the water is treated with ozone.

17 Claims, 3 Drawing Sheets

(51) Int. Cl.
*G01N 1/20* (2006.01)
*G01N 15/02* (2006.01)
*G01N 15/14* (2006.01)
*C02F 1/00* (2006.01)
C02F 103/34 (2006.01)
C02F 101/30 (2006.01)
G01N 1/40 (2006.01)

(52) U.S. Cl.
CPC ..... *G01N 15/0211* (2013.01); *G01N 15/1459* (2013.01); *C02F 2101/306* (2013.01); *C02F 2103/343* (2013.01); *C02F 2209/008* (2013.01); *C02F 2209/02* (2013.01); *C02F 2209/04* (2013.01); *C02F 2209/05* (2013.01); *C02F 2209/06* (2013.01); *C02F 2209/105* (2013.01); *C02F 2209/11* (2013.01); *C02F 2209/22* (2013.01); *C02F 2303/04* (2013.01); *G01N 2001/4088* (2013.01); *G01N 2015/1486* (2013.01)

(58) Field of Classification Search
CPC .......... C02F 2101/306; C02F 2209/105; C02F 2209/05; C02F 2209/04; C02F 2209/02; C02F 2103/343; C02F 2209/11; C02F 2209/22; C02F 1/44; C02F 1/4672; G01N 1/2035; G01N 15/1459; G01N 15/0211; G01N 2001/4088; G01N 2015/1486; G01N 1/20; G01N 1/40; G01N 1/4005; G01N 15/02; G01N 15/06; G01N 15/10; G01N 15/211; G01N 2001/4016; G01N 2015/1062; G01N 2015/1081; G01N 2015/1087; G01N 2015/149; B01D 61/14; B01D 61/20; B01D 61/22; B01D 2311/2634; B01D 2311/2692; B01L 2200/0631; B01L 2200/0652
USPC ........... 73/61.41, 61.59, 61.63, 61.71, 61.72, 73/863.23; 210/650, 651, 739, 745, 746, 210/760; 356/36, 38, 335–338; 377/11; 436/174, 176, 177, 178
See application file for complete search history.

(56) References Cited

U.S. PATENT DOCUMENTS

| | | | |
|---|---|---|---|
| 2005/0016929 A1 | 1/2005 | Kashkoush | |
| 2007/0151924 A1 | 7/2007 | Mir et al. | |
| 2008/0067133 A1* | 3/2008 | Bryant | .................... C02F 1/008 210/745 |
| 2008/0087076 A1 | 4/2008 | Busch | |
| 2008/0168828 A1* | 7/2008 | Endou | .................... B01D 61/18 73/61.72 |
| 2008/0289402 A1 | 11/2008 | Chowdhury | |
| 2010/0066547 A1* | 3/2010 | Chowdhury | ............ C02F 1/008 340/603 |
| 2010/0097605 A1* | 4/2010 | Murakami | ............. B01D 61/20 356/337 |
| 2011/0066382 A1 | 3/2011 | Adams | |
| 2012/0277902 A1* | 11/2012 | Sharpe | .................. B07C 5/3425 700/223 |
| 2013/0015137 A1* | 1/2013 | Urmenyi | ................ B01D 37/04 210/654 |
| 2013/0293873 A1 | 11/2013 | Bentien | |

FOREIGN PATENT DOCUMENTS

| | | |
|---|---|---|
| WO | 2011/061310 | 5/2011 |
| WO | 2013/091658 | 6/2013 |

OTHER PUBLICATIONS

Written Opinion of the International Searching Authority dated May 5, 2015 in International (PCT) Application No. PCT/SE2015/050113.

English translation of Search Report dated Apr. 26, 2017 in corresponding Chinese Application No. 201580007059.6.

* cited by examiner

METHOD AND DEVICE FOR ONLINE MONITORING OF WATER QUALITY

FIELD OF THE INVENTION

The present invention relates to the field of water treatment and monitoring of quality of water in a water distribution system.

BACKGROUND OF THE INVENTION

Access to water of good quality is of vital concern for mankind globally. Especially on the emerging markets the challenge is very real with many water stressed countries. The availability of clean and safe water is a major problem in both developed and developing countries. At present the world is facing difficult challenge in meeting the increasing demand of potable water systems due to population growth, urbanization, increasing pollution of water bodies from various industrial and agricultural activities, heavy rain, and drought caused by climate change and demands from various users (Vörösmarty et al, 2000; Lee et al. 2005; Moe et al, 2006; Coetser et al, 2007, Theron et al 2008). According to the WHO, more than 1 billion people, mostly in the developing countries, still do not have access to an adequate supply of drinking water (World Health Organization 2004) and as a result, the quality of health and welfare of vulnerable groups (children, the elderly and poor) are dependent on the availability of safe and affordable water supply (Theron et al, 2008; Theron et al, 2002).

The fact remains, though, that a growing human population demands clean and safe drinking water from the community. It is estimated that 2.2 billion people lack access to clean and safe water. There are 900 million water related sicknesses per year half of the world's hospital beds are filled with people suffering from water related diseases (World Health Organization), mostly affecting children and women. Every year two million children die or one every 15 seconds as a result of drinking contaminated water (World Health Organization). These are incredible numbers.

Municipal wastewater treatment plants which take care of household wastewater as well as industrial effluent are the main source of contamination to rivers and lakes. Treated and untreated water as well as overflows go directly to the nature and may pose a threat to water ecosystems in lakes and rivers. Water from lakes and rivers moreover is the source of drinking water.

Despite the fact that drinking water is our most common and valuable commodity there is a lack of practical real time monitoring and detection systems as well as proper treatment systems which address the need of detecting possible micro contaminants such as bacteria and parasites and pharmaceutical residues in drinking water. Improved surveillance and sampling systems together with effective treatment are needed to detect and avoid any sudden deterioration in water quality and to actuate proper measures, like effective disinfection or polishing.

There are several on line instruments available in the market today, e.g instruments for measuring TOC (total organic carbon), BOD (biological oxygen demand), ions, chlorine, DO (dissolved oxygen) and so on. The most common, though, in all the water treatment plants worldwide is to measure pH, temperature, turbidity and chlorine. These parameters are not processed and do not give any information about microbiological growth nor danger for parasites like *Cryptosporidium* and *Giardia* nor increased organic matter and so on.

Two important examples of pathogenic microorganisms that may be transmitted to humans by contaminated water are *Giardia* and *Cryptosporidium*. *Cryptosporidium* oocysts are common and widespread in ambient water and can persist for months in this environment. The dose necessary to infect humans (i.e. the infectious dose) is low, and a number of waterborne disease outbreaks caused by this protozoan have occurred all over the world, and continue to do so. The problem is aggravated by the fact that *Cryptosporidium* is resistant to commonly used water disinfection practices such as chlorination and by the fact that presently there are no drugs effective in preventing or controlling gastroenteritis caused by *Cryptosporidium*.

Giardiasis is the most commonly reported intestinal protozoan infection worldwide. The World Health Organization estimates 200 million people are infected each year. Human infections with *Giardia* have been reported in all of the major climatic regions, from the tropics to the arctic. *Giardia* cysts are ubiquitous in surface waters of all qualities. Because *Giardia* infections are widespread in human and animal populations, contamination of the environment is inevitable and cysts have been detected in even the most pristine of surface waters.

The human related source of *Cryptosporidium* and *Giardia* is treated wastewater. Today there is no surveillance system which monitors microbiological discharge to the nature, i.e. lakes and rivers. Treated or untreated wastewater with microbiological load of varying concentration mixes with lake and river water, which is referred to as "natural dilution".

Another emerging contamination which, together with pathogens, causes an environmental load on water sources are residues of pharmaceutical products, originating as well from the pharmaceutical industry as from human consumption and animal antibiotics. Furthermore, personal care products have also become an environmental issue of today.

These residues cling to micro contaminants, such as bacteria and protozoa, in a flow of water and cause damage to environment; and ultimately affect human beings. Indeed, wastewater containing drug residues lead to contamination of source water, used for production of drinking water. It appears that pharmaceutical/personal care product residues are an emerging environmental problem on a global scale.

As used herein, the term wastewater is any water that has been adversely affected in quality by anthropogenic influence. It comprises liquid waste discharged by domestic residences, commercial properties, industry, and/or agriculture. One example of wastewater is municipal wastewater.

Improved sensitive surveillance systems with sampling and inactivation of contaminants to ensure the proper application of different water cleanliness are needed to detect these contaminants. Sudden deterioration in water cleanliness due to the presence of pathogens and pharmaceutical residues in treated wastewater and source/lake water is the challenge of today and of tomorrow.

Treatment of wastewater is necessary to reduce the organic loads and suspended solids, to limit environmental pollution and to avoid health risks. The existing treatment methods used in municipal wastewater are physical, chemical and biological process. The physicochemical process involves primary and secondary sedimentation using chemical precipitation, chemical coagulation, and removal of suspended solids and dissolved matter and filtration. The biological treatment mainly involves activated sludge and biomass production.

This is a very complex system and the complete process takes about 24-40 hours involving various steps in wastewater treatment (Tansel, 2008). The term "total organic carbon" generally refers to carbon bound in organic material derived from decaying vegetation, bacterial growth, and metabolic activities of living organisms or chemicals. High organic carbon in water is an indicator that microbiological growth possible.

Pathogens like *Cryptosporidium, Giardia*, hookworm, amoebas and bacteria and pharmaceutical residues may be present in untreated or insufficiently treated wastewater and if this water reaches the river/lake, the water becomes unfit as a source for drinking water source as there no monitoring system which gives information about the contamination.

New technologies are being developed for wastewater treatment, like MBR (membrane bio reactors), separations of organics by nano technology, ultra and nano filtration, and so on.

The focus in wastewater treatment of today is to remove Nitrogen and Phosphorus and to convert waste to energy. Nanotechnology and MBR membrane bio reactors of different size and capacity have been identified and developed to provide solutions for many of the difficulties associated with water treatment and quality (Theron et al, 2008)

Considering the importance of potable drinking water globally, and keeping in mind concerns regarding the viability of recent practices for meeting the rising water demands, there is a pressing need to develop novel technologies and materials that will tackle the challenges associated with cleanliness of safe drinking water, recycled water and source and lake water that will be used for different purposes. While new water treatment technologies are being developed today, there is a need for a novel cost effective, user-friendly, robust and more efficient polishing system which in one step can remove/inactivate parasites, such as *Cryptosporidium* and *Giardia* as well as pharmaceutical residues in the treated flow of water.

Presently, the normal method of detection of microorganisms in water is to collect 500 ml of random water samples in sterile bottles and then take less than a drop of each sample for analysis. In order to determine the presence of any microorganism, the sample may be subjected to incubation on an agar plate followed by counting of colony forming units on the plate. It goes without saying that such methods have several drawbacks. One drawback is the high risk of undetected contamination due to the random character of sampling. Another drawback is the low sensitivity due to the small volume analyzed: only a fraction of a drop is used for analysis and evaluation out of a 500 ml sample.

For parasites, no standard regular analysis is performed due to high cost and complexity in analyzing. Some bigger water treatment plants analyze samples once a month or once a year. The analysis takes several weeks with high cost. Furthermore, more than 100 liters of water is needed to perform a proper analysis.

However, microbiological contamination is prone to occur from time to time in a water distribution system, for many reasons, for example if, for some reason, treatment of water fails or biofilm loosens in a distribution system. Such microbiological contamination may exist for a very short time, e.g. 5 to 60 seconds, or for a longer time, before the water quality returns to normal again. The state of the art random sampling is not suitable to catch this type of microbiological contamination. Contamination of this nature may occur several times a day/week/month and pass through unnoticed but cause more or less severe health problems at the consumer's end.

U.S. Pat. No. 7,891,235 discloses a method for monitoring water quality in a water system. In this system, a water pipe is provided for conveying water therein. A particle sensor is in operative engagement with the water pipe. The particle sensor continuously counts particles in the water of the water pipe. The particle sensor triggers the taking of a water sample only when the particle count reaches a predetermined level.

International application No. WO/2002/017975 discloses a method of assessing the presence of ozone consuming agents on the surface of an object or within an enclosed volume, by providing a fluid containing ozone, bringing the fluid into contact with the object or introducing the fluid into the enclosed volume, measuring the concentration of ozone in the fluid and evaluating the presence of the ozone consuming agents as a function of the measured ozone concentration. In particular the method is applicable as a method of assessing the cleanness, expressed in terms of the essential absence of ozone consuming agents, of a surface or volume.

International application No. WO/2011/061310 discloses a water supply and monitoring system comprising a first water pipe, a particle sensor for sensing particles in the water at a first location in said pipe; a second pipe, in fluid communication with the first pipe by means of a first valve disposed at a second location on the first pipe downstream of the first location; a third pipe, in fluid communication with the first pipe at a location between the first and second locations; a second valve, allowing water conveyed by the first pipe to flow into the third pipe. Also described is a method using said arrangement, comprising determining a content of particles in the water within a particle size interval within the range of from 0.1 to 100 micrometers in the first pipe; triggering closure of the first valve and opening of the second valve when the determined content of particles is higher than a predetermined level, whereby water flowing in the first pipe is diverted from the second pipe into the third pipe.

SUMMARY OF THE INVENTION

One object of the present invention is to provide means and methods for the final treatment of water as well as monitoring, sampling and classifying of the contaminants (pharmaceutical residues as well as parasites *Cryptosporidium* and *Giardia*) in real time whereas the use of chemicals is substantially reduced and classified clean water for different purposes can be obtained.

Another objective of the invention is to provide correct water sample of precise volume of water with the information of contamination.

By the method of the invention, water sampling is advantageously performed at the occurrence of contamination, instead of randomly, and for as long as the contamination persists.

Another objective of this invention is to concentrate in real time the volume of water sampled without destroying the contaminants.

Still another object of the present invention is to provide means and methods for the treatment of water wherein viruses, bacteria, algae, protozoa and parasites are effectively removed from the water.

Another object of the invention is to provide means and methods for the plant management to make quick decision in order to avoid contamination in the water bodies.

Another object of present invention is to provide means and methods for reducing the content of microbiological and small particle (e.g. of drug residues) contaminants in water bodies.

Another object of present invention is to provide means and methods for reducing the content of chemical contaminants, such as drugs, personal care products, pesticides, insecticides etc. in water such as municipal (tap) water, treated wastewater or source water.

Still another object of the present invention is to provide means and methods for improved monitoring of water quality.

Still another object of the present invention is to provide means and methods for improved detection of even very low amounts of microbial contamination in water.

Another object of the present invention is to provide a water treatment process with real time quality control maintaining high level of efficiency, security and water safety.

Another object of the present invention is to provide a method for monitoring the quality of water flowing in a water distribution system wherein water samples are captured in connection to the occurrence of contamination.

Another object of the present invention is to provide a method for monitoring the quality of water wherein sampling of the water is triggered by the detection of presence of contaminants in the water.

According to a first aspect, therefore, there is provided a method for monitoring quality of water flowing in a pipe, by (i) diverting a flow of water from the pipe into a laser particle counter that continuously counts particles within a particle size interval $S_n$ in the diverted flow of water, so as to determine for each time $t_i$ a number $c_i''$ of particles within said size interval per volume of water, comparing $c_i''$ with a previously determined reference value $c_{ref}''$ for the number of particles per volume of water flowing in the pipe; and taking a sample of the water from the pipe when $c_i''$ exceeds a predetermined threshold value $TV_A''$ for more than a predetermined length of time $t_A''$, (ii) diverting a flow of water from the pipe into a unit that separates the flow into a fraction of higher particulate concentration within particle size interval $S_n$ and a fraction of lower particulate concentration within said particle size interval, and taking a sample of at least one of said fractions when $c_i''$ exceeds a predetermined threshold value $TV_B''$ for more than a predetermined length of time $t_B''$; and (iii) sending an alarm signal when $c_i''$ exceeds a predetermined threshold value $TV_C''$ for more than a predetermined length of time $t_C''$.

The alarm signal e.g. may be an electronic signal to a computer or a cell phone.

One preferred embodiment comprises adding ozone to the water flowing in the pipe when $c_i''$ exceeds a predetermined threshold value $TV_D''$ for more than a predetermined length of time $t_D''$. The addition e.g. may be made by allowing water flowing in pipe to pass through a tank or chamber, into which tank or chamber ozone is also admitted, and allowing the water to exit from the tank after a suitable treatment time.

The size of the particles counted by the counter generally ranges from about 0.1 μm up to about 100 μm. In one embodiment, the particle counter continuously counts particles within a particle size interval $S_1$ of from e.g. 0.5 to 3 μm to provide a number $c_i^1$ of particles within said size interval per volume of water. This embodiment preferably comprises taking a sample of the permeate flow of the filtering unit when $c_i^1$ exceeds a predetermined threshold value $TV_B^1$ for a more than predetermined length of time $t_B^1$.

In one embodiment, the particle counter continuously counts particles within a particle size interval $S_2$ of from e.g. 3 to 25 μm to provide a number $c_i^2$ of particles within said size interval per volume of water. This embodiment preferably comprises taking a sample of the concentrate flow of the filtering unit when $c_i^2$ exceeds a predetermined threshold value $TV_B^2$ for more than a predetermined length of time $t_B^2$.

The samples taken preferably are subjected to one or more physical, chemical, biochemical or microbiological analyses.

One embodiment further comprises continuously measuring at least one further physical or chemical parameter of the flow of water, e.g. a parameter selected from dissolved solids in the water, dissolved oxygen, pH, electrical conductivity, temperature and turbidity.

DETAILED DESCRIPTION OF THE INVENTION

Figure 1:
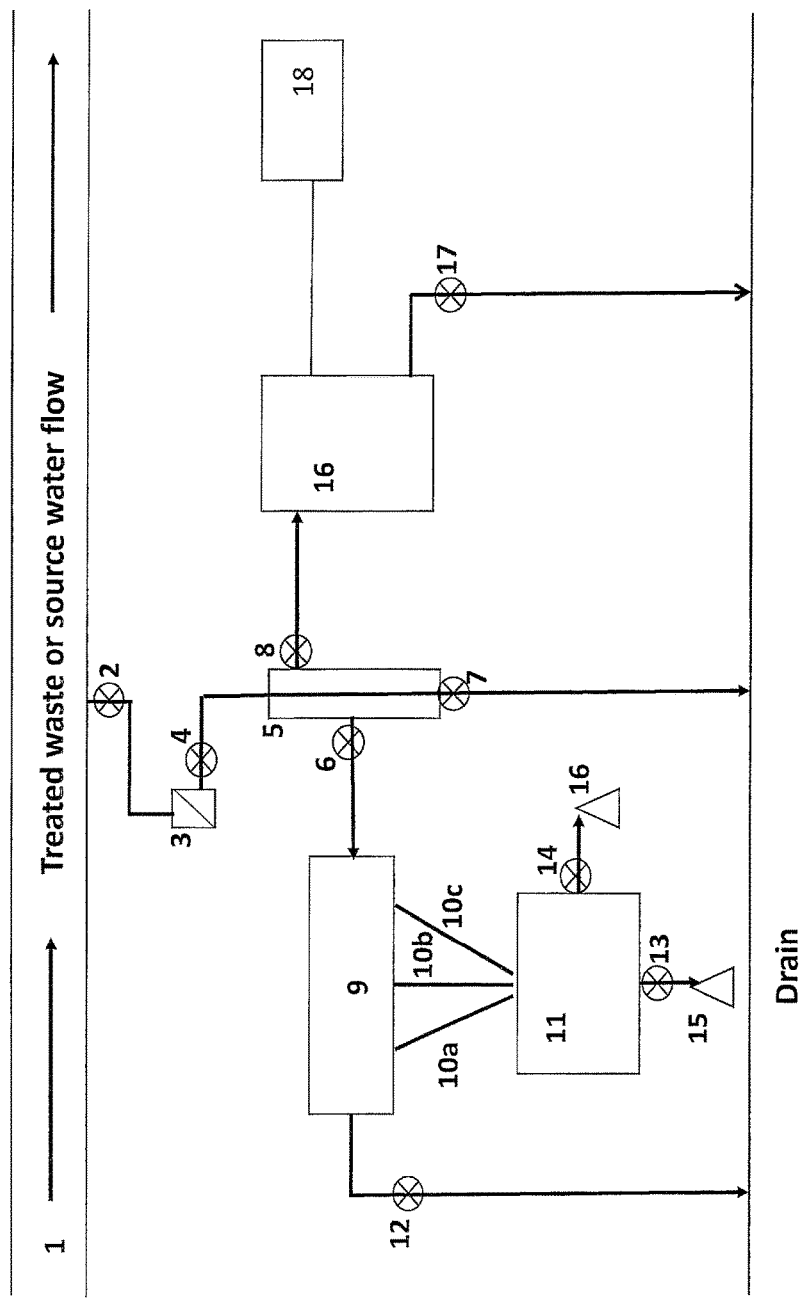
FIG. 1 is a schematic representation of a water monitoring system of the present invention.

The method of the invention comprises diverting a flow of water from the pipe into a particle counter that continuously counts particles within a particle size interval $S_n$ in the diverted flow of water, so as to continuously provide information about the number $c_i''$ of particles within said size interval, per volume of water.

The flow of water diverted from the water flowing in the pipe e.g. is a flow of 5 l/min to 10 l/min. The flow of water is diverted from the pipe at any suitable location. For example, if the water is wastewater to be discharged through an outlet, into a recipient, the flow should be diverted at any location upstream of the outlet.

At least part of the diverted flow passes through a laser particle counter, where particles present in the water flow are continuously counted. The laser particle counter may be any conventional liquid phase particle counter, e.g. laser counter operating within a wavelength of 330 to 870 nm, such as e.g. WPC-21, commercially available from HACH LANGE, MetOne and others.

The particles that are counted generally have a particle size within a range of from 0.1 μm to 100 μm, e.g. from 0.2 μm to 50 μm, or from 0.5 μm to 25 μm, e.g. a size interval generally corresponding to microbiological contaminants such as viruses, bacteria and protozoan parasites, and to small particulate organic and inorganic matter, e.g. drug residues. Within this group, bacteria and viruses generally are at the small size end, while parasites generally are at the large size end. Thus, particle counts within a size interval of from 0.1 to 5 μm, e.g. within a size interval of from 0.2 to 5 μm, or within a size interval of from 0.5 to 3 μm will give an indication of the presence of viruses and bacteria in the water, and may also give an indication of the presence of drug residues. On the other hand, particle counts within a size interval of from 3 to 100 μm, or from 3 to 50 μm, e.g. from 3 to 25 μm, e.g. from 5 to 100 μm, or from 5 to 50 μm, e.g. from 5 to 25 μm, or from 10 to 100 μm, e.g. from 10 to 50 μm, or from 10 to 25 μm will give an indication of the presence of parasites in the water, and may also give an indication of the presence of drug residues. The drug residues may be both particulate drug residues, and drug substances attached to microbe particles.

Thus, in one embodiment, particles are continuously counted within a particle size interval $S_1$ corresponding generally to the size of viruses and bacteria, e.g. a size interval of from about 0.1 µm to about 5 µm, or from about 0.2 µm to about 5 µm, e.g. from about 0.5 µm to about 3 µm; e.g. from about 0.1 µm, or from about 0.2 µm, or from about 0.3 µm, or from about 0.4 µm, or from about 0.5 µm, to about 5 µm, or to about 4 µm, or to about 3 µm or to about 2 µm, so as to continuously provide information about the number $c_i^1$ of particles within said size interval per volume of water.

Further, in one embodiment particles are continuously counted within a particle size interval $S_2$ corresponding generally to the size of microbiological parasites, e.g. a size interval of from about 3 µm to about 100 µm, or from about 3 µm to about 50 µm, e.g. from about 3 µm to about 25 µm, e.g. from about 3 µm, or from about 4 µm, or from about 5 µm, or from about 6 µm, or from about 8 µm, or from about 10 µm, to about 100 µm, or to about 80 µm, or to about 50 µm or to about 25 µm, so as to continuously provide information about the number $c_i^2$ of particles within said size interval per volume of water.

Preferably particles are counted within or over both particle size intervals $S_1$ and $S_2$. In some embodiments, particles may be counted within several different size intervals, e.g. subintervals of any of the above mentioned intervals, or any other interval corresponding to microbial contamination or other particulate contamination.

In the inventive method, the number of particles $c_i^n$ within a given size interval $S_n$ is continuously compared with a pre-determined reference value $c_{ref}^n$ for the number of particles within this size interval per volume of water flowing in the pipe.

The number $c_{ref}^n$ preferably is determined for each type of setting and water, and may be e.g. a value obtained by counting particles within the particle size interval $S_n$ in a flow of water diverted from the pipe during a preliminary period, of e.g. 1 hour, 10 hours, 1 day or even 1 week or longer, whereby a mean or "baseline" value for the particle count is obtained, as well as an indication of the normal amplitude of fluctuations around this mean value, allowing a Gaussian distribution around a mean value to be calculated.

Determination of $c_{ref}^n$ may be repeated regularly, e.g. once a day, once a week, once a month or once a year, or at any other selected time interval, or when considered necessary due to a change in any condition, e.g. environmental conditions or method of treatment of the water etc.

Other ways of determining $c_{ref}^n$ are conceivable and considered well within the scope of the person of ordinary skill. For example, in some embodiments, $c_{ref}^n$ is continuously determined as a mean value of measured particle counts within the size interval during a time period preceding the time $t_i$.

In the method of the invention a sample of the water is taken when $c_i^n$ exceeds a predetermined threshold value ($TV_A^n$) for more than a predetermined length of time $t_A^n$ (the "threshold time"). Very advantageously, the sampling is automatically triggered when the above condition is fulfilled. $TV_A^n$ preferably is selected using the Gaussian distribution around $c_{ref}^n$. For example, in order to select a suitable $TV_A^n$, the standard deviation $\sigma_n$ associated with $c_{ref}^n$ may be calculated, and $TV_A^n$ may be selected as a function of $\sigma_n$, i.e. $TV_A^n = c_{ref}^n + q \times \sigma_n$, where q may be a number of from e.g. 1 to 10, e.g. from 1.5 to 5, or from 2 to 4. However, it should be realized that $TV_A^n$ (as well as any other of the threshold values referred to herein) may also be selected by any other suitable method, e.g. by previous experience, by studying the amplitude of variations for a period of time in the particular setting, or as a pre-determined factor of $c_{ref}^n$, e.g. of a factor of from 2 to 1000, or a factor of from 4 to 500, or a factor of from 5 to 200, or a factor of from 10 to 100, or a factor of from 20 to 50.

It will be realized that the particle count will be subject to normal fluctuations, and at irregular intervals, short lived spikes may occur. Therefore, in order to avoid "false positives", a taking of a sample of the water preferably should be triggered only when $c_i^n$ has exceeded a predetermined threshold value $TV_A^n$ for more than a predetermined length of time $t_A^n$, of e.g. 5 seconds to 1 hour; e.g. 10 seconds to 0.5 hour; or 0.5 minute to 10 minutes; or 1 minute to 5 minutes.

In some embodiments, several threshold values $TV_A^n$ are selected for any one particle size interval, with corresponding threshold times $t_A^n$, where a higher threshold value is associated with a shorter threshold time $t_A^n$. For example, for a threshold value $TV_A^n = c_{ref}^n + q\lambda\,\sigma_n$, the corresponding threshold time $t_A^n(q)$ may be selected so that $$t_A^n(q) = \frac{1}{q} \times t_A^n(1).$$

Preferably, the sampling will be repeated for as long as the particle count remains higher than a predetermined threshold value, which may be the same as $TV_A^n$ or different. For example, the sampling may be repeated at least until the particle count has returned to a value lower than $c_{ref}^n + q' \times \sigma_n$, where q' e.g. is 0.5, 1, 1.5, or 2.

The water sample is taken at a location selected so as to give a sample representative for the water flowing in the pipe. In some embodiments of the invention, water samples are withdrawn directly from the pipe. For example, water samples may be withdrawn using a modular based sampler including a plurality of sterile sample bottles, e.g. 4 sterile sample bottles. Sampling and sample preservation preferably is performed following standards for water sampling, such as the relevant ASTM standards.

During a contamination time of e.g. 5 to 60 seconds or 120 seconds or for a longer time, water samples are collected until the particle count reach a predetermined threshold value, and optionally also until any other measured parameter reaches a predetermined threshold value. For example, 6 samples may be collected per hour, for as long as considered necessary or for as long as any threshold value is exceeded. This gives better statistics and confidence in analyzing results.

The method of the invention further comprises diverting a flow of water from the pipe into a unit that separates the flow into a fraction of higher particulate concentration within particle size interval $S_n$ and a fraction of lower particulate concentration within said particle size interval, and taking a sample of at least one of said fractions when $c_i^n$ exceeds a predetermined threshold value $TV_B^n$ for more than a predetermined length of time $t_B^n$.

$TV_B^n$ and $t_B^n$ may be selected in the same way as $TV_A^n$ and $t_A^n$, using the previously determined reference value $c_{ref}^n$ and associated the Gaussian distribution of particle counts. In some embodiments, $TV_B^n$ and $t_B^n$ are identical with $TV_A^n$ and $t_A^n$.

In some embodiments, a sample is taken from the fraction of higher particulate concentration within particle size interval $S_n$. In some embodiments, a sample is taken from the fraction of lower particulate concentration within particle size interval $S_n$.

A unit—or device—that separates the flow into a fraction of higher particulate concentration within particle size interval $S_n$ and a fraction of lower particulate concentration e.g. may be a filtering unit or a centrifuge.

For example, the method may comprise diverting a flow of water from the pipe into a filtering unit that filters the water to provide a permeate flow and a concentrate flow, and taking a sample of at least one of the permeate flow and the concentrate flow when $c_i^n$ exceeds a predetermined threshold value $TV_B^n$ for more than a predetermined length of time $t_B^n$.

In some embodiments, a sample is taken from the concentrate flow. In some other embodiments, a sample is taken from the permeate flow.

A filtering unit e.g. may be a conventional ceramic water filter, such as the filter cartridges sold by e.g. Doulton USA.

By selecting a filtering unit having a suitable cut-off pore size, e.g. a cut-off pore size of about 3 μm, two fractions are retrievable, i.e. a first fraction containing particles larger than the cut-off size, such as protozoan parasites like *Cryptosporidium* or *Giardia*, and a second fraction containing particles smaller than the cut-off size, e.g. bacteria, viruses and particulate drug residues. Samples may be taken from either one fraction, but preferably are taken from both fractions.

For example, a suitable system for concentrating small to medium volumes (e.g. 50 ml to 10 l) of sample consists of a membrane capillary, pressure gauge, a ceramic membrane module and a tank. The water sample collected in the tank is forced through the membranes in the membrane module by the pump and recirculated back to the tank. By this cross flow ceramic membrane filtration two fractions are obtained—one is permeate and other is concentrate.

In some embodiments, at least one fraction, e.g. the concentrate, is subjected to optical monitoring, PCR analysis or traditional incubation. In some embodiments, the flow diverted into the ceramic filtering unit is recirculated therein, to obtain a concentrating effect, and samples are taken at regular intervals from the recirculating fluid, e.g. as long as the particle count exceeds a threshold value, such as $TV_B^n$. This may be particularly useful to detect the presence of parasites that are pathogenic at even very low concentrations, i.e. having a low infectious dose, such as *Cryptosporidium* or *Giardia*.

The samples taken in the method of the invention may be analyzed directly or stored for later analysis. Samples stored for later analysis preferably are kept at low temperature, e.g. a temperature below 8° C., such as a temperature of from 4 to 6° C., at least until the time of analysis.

Analysis of the sample may be by any microbiological, biochemical, chemical or physical method for analyzing water, as is well-known to the person of ordinary skill within the field, e.g. by following appropriate water testing standards according to ASTM.

The method of the invention also comprises the automatic sending of an alarm signal when $c_i^n$ exceeds a predetermined threshold value $TV_C^n$ for more than a predetermined length of time $t_C^n$. $TV_C^n$ and $t_C^n$ may be selected according to the same principles as $TV_A^n$ and $t_A^n$ and in some embodiments are identical with $TV_A^n$ and $t_A^n$ or with $TV_B^n$ and $t_B^n$.

The alarm signal preferably is an electronic signal, e.g. sent via Internet to a computer or a cell phone, such as a smartphone.

In some embodiments, an alarm signal also is sent at the end of a pollution episode, i.e. when the particle count within a size interval decreases to and below a threshold value.

Further events may be linked to the alarm signal, such as interruption of the water flow in the pipe or the deviation of the flow e.g. to a purification system or to a recirculation loop, or back to the treatment plant.

In some embodiments, the method comprises adding ozone to the water flowing in the pipe when $c_i^n$ exceeds a predetermined threshold value $TV_D^n$ for more than a predetermined length of time $t_D^n$. $TV_D^n$ and $t_D^n$ may be selected in the same way as $TV_A^n$ and $t_A^n$ and in some embodiments are identical with $TV_A^n$ and $t_A^n$, or with $TV_B^n$ and $t_B^n$, or with $TV_C^n$ and $t_C^n$.

The addition of ozone to the water flowing in the pipe is triggered automatically and preferably will continue as long as $c_i^n$ exceeds a predetermined threshold value, which may be identical or not with $TV_D^n$.

The ozone addition preferably is achieved by allowing the water flowing in the pipe to pass through a chamber or tank to which ozone may also be added at a signal triggered by the particle count.

In some embodiments, about 0.05 g, 0.1 g, 0.2 g, 0.5 g, 1 g, or 2 g or less than 5 g of ozone per $m^3$ of water is added to the water flowing in the pipe in order to cause degradation of drug residues and other chemical substances, e.g. residues from personal care products, as well as microorganisms present in the water. At such a low concentration of ozone, it has been found that no harmful by products of the ozone treatment remains in the water, whereas the total organic carbon (TOC) and discoloring of the water may be reduced by e.g. 20% and 50%, respectively. The bacterial count in wastewater may be reduced to zero by such ozone treatment.

In some embodiments, the ozone concentration in treated water is from about 0.05 ppm to about 5 ppm, e.g. from about 0.05 ppm to about 2 ppm, or from about 0.1 ppm to 2 about ppm.

An ozone treatment time of 5 minutes to 2 hours, e.g. 10 minutes to 1 hour, is generally sufficient, but shorter or longer treatment times may be applied if considered suitable, considering e.g. the level of pollution.

In some embodiments, water is continuously treated by addition of ozone, and the amount of ozone added to the water is adjusted as a function of the amount of particles measured ($c_i^n$). For example, when $c_i^n$ is lower than $TV_D^n$, a low amount of e.g. 0.01, or 0.02, or 0.05 mg ozone/$m^3$ of water is added, which amount is automatically raised when $c_i^n$ exceeds $TV_D^n$.

Generally, concentrations of ozone much higher than the above-mentioned are considered necessary in order to achieve a satisfactory destruction of pollutants, such as pharmaceutical residues, in water. In contrast, in one very advantageous embodiment of the invention, an astonishingly efficient destruction of various chemical residues is achieved by addition of only small amount of ozone. Such chemical residues may be of any origin, pharmaceuticals pesticides, insecticides, personal care products etc. The efficient destruction is achieved by adding ozone to the wastewater only after the wastewater has undergone other purification treatment steps to remove gross contaminants that would otherwise destroy the added ozone.

In some embodiments, ozone is added to the water using technology described in WO/2002/017975 (vide supra), the contents of which is incorporated herein in its entirety. In particular, the mixing chambers and tanks described therein allow for a very efficient mixing of ozone and water, which will even further increase the ozone efficacy in destroying unwanted residual substances in the water at a very low amount of ozone added.

In some embodiments, the method of the invention further comprises
- continuously measuring at least one further physical or chemical parameter of the water,
- comparing the measured value P of the physical or chemical parameter with a reference value Pref for the parameter previously determined for the water,
- sending an alarm signal when P differs from Pref by more than a predetermined threshold value $\Delta_P$ for more than a predetermined length of time $t_P$.

For each parameter, Pref may be determined applying the same principle as in determining $S_n$, and the threshold value $\Delta_P$ and the threshold time may be selected as described herein above for $TV_A''$ and $t_A''$.

For example, total dissolved solids, ORP (oxidation reduction potential), dissolved oxygen, pH, turbidity, oxygen demand, electrical conductivity, temperature or any other parameter of the water flowing in the pipe may be determined, by measuring directly on-line (in the pipe), or by taking a sample from the pipe, or e.g. by diverting one or more further flows from the pipe, e.g. by sampling or on-line analysis of the flow directed to the particle counter and/or the flow directed to the fractionating unit. The person of ordinary skill in the art will be well capable of selecting suitable means and methods for performing the elected analysis, e.g. by applying any of the methods indicated as ASTM standard methods for water analysis, cf. e.g. http://www.astm.org/Standards/water-testing-standards.html#D19.24.

Thus, the monitoring system of the invention preferably also comprises at least one of:
- a TDS (total dissolved solids) sensor capable of measuring the total dissolved solids in a flow of water in a range of 0-5000 ppm (mg/l);
- an electrical conductivity sensor keeping track of the electrical conductivity in the water within a range of 0-10000 micro S; and
- a thermometer for measuring the temperature of the water.

In some preferable embodiments, the system comprises all three sensors, attached to the water pipe and all the information of the measured values are computed and stored in a database in real time.

One embodiment of the invention is a system for monitoring a flow of e.g. treated wastewater or source water (e.g. water from a lake or river) as illustrated in FIG. 1, and a method wherein such as system is used. In this system, water is withdrawn from a flow of treated wastewater or source water flowing in a pipe 1 by means of on/off valve/flow regulator 2 and allowed to flow through a prefilter unit 3, followed by on/off valve/flow regulator 4.

In distributor unit 5, e.g. a manifold, the water flow is divided into three different flows, passing through on/off valve/flow regulators 6, 7 and 8, respectively.

Water flowing through valve 6 enters sampling manifold 9. Manifold 9, e.g. of the Bürkert type, preferably has an inner design such as to avoid corners and threads and the inner material is made e.g. of electro polished stainless steel or inert plastic material. The main advantage of this selection of design and material is that it will create a minimum growth of bacteria and biofilm inside the manifold which otherwise is commonly occurring. Manifold 9 is easy to take out and clean even under running conditions. For example, manifold 9 may be cleaned using a gaseous flow containing ozone at a concentration of about 30-50 ppm, or an aqueous flow containing ozone dissolved at a concentration of 0.3-0.5 mg/l, or any other means for disinfection used in the food and medicinal field, e.g. chemical disinfection.

Manifold 9 comprises four outlets, i.e. outlets 10a, 10b, 10c and outlet/valve 12. Water leaving sampling manifold 9 through outlets 10a, 10b, and 10c flows into ceramic filter unit 11 or to different sampling bottles (not shown). In ceramic filter unit 11, water is filtered through a ceramic membrane (not shown), to provide a permeate and a concentrate. On/off valve/flow regulator 13 allows to withdraw sample 15 of the permeate from the ceramic membrane and on/off valve/flow regulator 14 allows to withdraw samples 16 of the concentrate. Water leaving the sampling manifold 9 through valve 12 is discharged to a drain for the water.

Water leaving distributor 5 through valve 7 is discharged directly to the drain, whereas water leaving distributor 5 through valve 8 enters monitor 16, containing sensors/detectors and communication system (not shown), communicating, e.g. via the Internet, with computer 18. The sensors/detectors of monitor 16 permit to determine various parameters of the water, such as total dissolved solids, particle count over various size intervals, total particle concentration, ionic strength, pH, temperature, TDS, dissolved oxygen etc. The computer 18 may also gather other information, such as weather information from different agencies. Water leaving the monitor 16 through valve 17 is discharged to a drain.

The system illustrated in FIG. 1 also may be applied e.g. to drinking water in a municipal distribution line, in which case prefilter 3 may be omitted.

The system illustrated in FIG. 1 can be stationary or portable (except for the pipe 1, which is not generally part of the system).

In the method for monitoring water of the present invention, water samples are withdrawn from the water pipe, e.g. at a signal from the particle counter, as described herein above. In one embodiment, water samples are withdrawn using a modular based sampler including 4 sterile sample bottles and/or filters. The bottles preferably contain 10 mg sodium thiosulfate according to standard. The sampler has a manifold which is at the top of the sampler and connected to the main distribution pipeline. Through the sampler there is a continuous flow of 5 l/min which gives always fresh flowing water.

On the manifold, e.g. of the Bürkert type, 4 electrical valves are mounted, having the function of opening and closing at a given signal. The signal to open or close comes from a relay which will be activated when triggered, e.g. by an SMS message and/or direct remote command from one main body which may stand nearby or up to several kilometers away.

The manifold has an inner design such as to avoid corners and threads and the inner material is made e.g. of electro polished stainless steel or inert plastic material. The main advantage of this manifold is that it will create a minimum growth of bacteria and biofilm inside the manifold which otherwise is normal. The manifold is easy to take out and clean even under running conditions. For example, the manifold may be cleaned using a gaseous flow containing ozone at a concentration of about 30-100 ppm, or an aqueous flow containing ozone dissolved at a concentration of 0.3-0.5 mg/l, or any other means for disinfection, e.g. chemical substances, used in the food and medicinal field.

The sampler can be placed on a table or wall mounted. Several such samplers can be attached at different locations at the distribution network.

The sampler preferably should include a cooling chamber that keeps the temperature at a low temperature, of e.g. 4-6° C.

Sampled water can be e.g. 100 ml, 250 ml, 500 ml, 1000 ml, or even 10000 ml, and though sampling preferably is automatically made, also manual sampling is possible. Samples, having undergone filtration/concentration or not, may be analyzed by, for example, incubation, PCR or optical fluorescence technology or biochemically.

For example, a sample taken either from any of the flows diverted from the pipe, e.g. a sample from the filtering unit, and/or a sample taken directly from the pipe, may be analysed for the presence of protozoa, e.g. *Cryptosporidium* and/or *Giardia*, as well as for the presence of bacteria, such as bacteria selected from any of the commonly used bacterial contamination indicator organisms, such as coliform organisms, e.g. fecal coliform bacteria.

Figure 2:
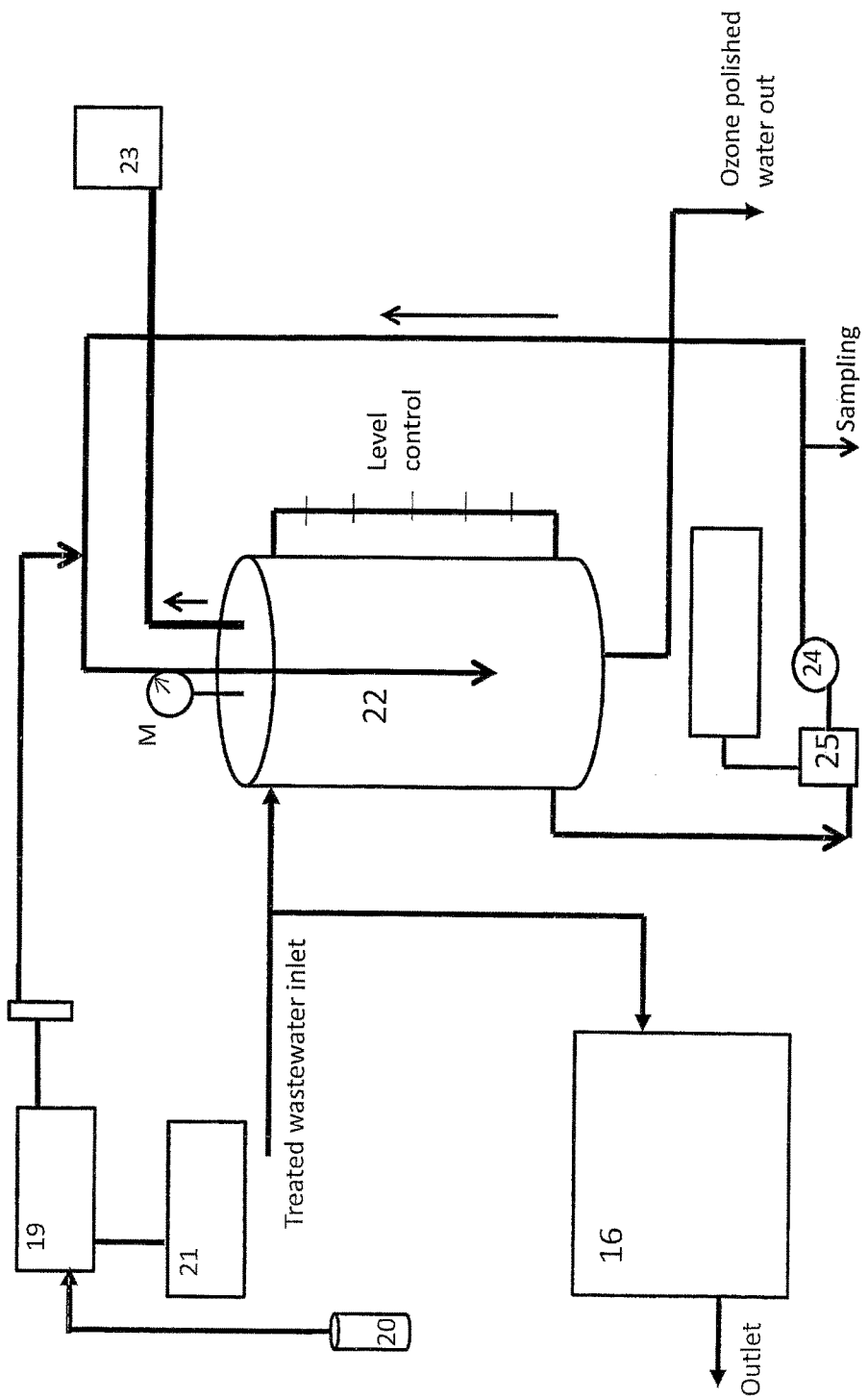
FIG. 2 is a schematic representation of an online ozone water treatment system of the present invention.

The system of the invention preferably also comprises means for ozone treatment of the water. FIG. 2 represents a schematic overview of an ozone treatment system of the invention. In FIG. 2, monitoring system 16 receives water diverted from a pipe (not shown), from which pipe also a flow is diverted to an ozone treatment system. The system comprises an ozone generator 19, receiving oxygen from an oxygen cylinder 20 and regulated by an ozone gas monitor 21. Water, which in the case illustrated in FIG. 2 is treated wastewater, is conveyed into an ozone treatment tank 22, into which tank ozone from ozone generator 19 is fed. Tank 22 is equipped with a level control for sensing the level of water in the tank and a pressure gauge (M) for the water pressure in the tank.

From tank 22, excess ozone is led to ozone destructor 23. Ozone treated water is transported by pump 24 from tank 22 into monitor 25 which measures the remaining ozone. By sampling of ozone treated water, the level of remaining pollution, e.g remaining amount of chemicals or microbiological particles, may be determined. If the quality is satisfactory water is allowed to exit from the ozone cleaning system at ("Ozone polished water out"). The water also may be returned to the tank 22 for further ozone treatment, e.g. if the sampling shows that the remaining level of pollution remains too high.

The invention is further illustrated in the following non-limiting Examples.

Example 1

From a flow of treated wastewater running in a pipe, a flow of 5 l/min is diverted into laser counter operating at a wavelength of from 330 to 870 µm, to continuously count particles over a size interval of from 0.5 to 25 µm. A further flow of water from the pipe is diverted into a ceramic filtering unit and is separated into a permeate flow containing particles capable of passing through filter pores having a diameter of about 5 µm as well as dissolved substances, and a concentrate flow containing particles that have not passed through the pores of the filter.

At time t, the particle count within the small particle size range of 0.5 to 3 µm suddenly increases and remains over a preselected threshold value of 1000 particles/l for more than a preselected threshold time of 1 minute. This triggers the taking of a 200 ml sample from the permeate flow.

The particle count remains higher than 1000 particles/l in the flow for a period of 1 hour and then returns to a value below this threshold value. During this time period, in total 5 further samples are collected from the permeate flow and stored at a temperature of 5° C. or subjected to microbiological analysis for the presence of coliform organisms, respectively.

Example 2

From a flow of treated wastewater running in a pipe, a flow of 5 l/min is diverted into laser counter operating at a wavelength of from 330 to 870 µm, to continuously count particles over a size interval of from 0.5 to 25 µm. A further flow of water from the pipe is diverted into a ceramic filtering unit and is separated into a permeate flow containing particles capable of passing through filter pores having a diameter of about 5 µm as well as dissolved substances, and a concentrate flow containing particles that have not passed through the pores of the filter.

At time t, the particle count within the small particle size range of 0.5 to 3 µm suddenly increases and remains over a preselected threshold value of 10000 particles/l for more than a preselected threshold time of 0.5 minute. This triggers the taking of a 200 ml sample from the permeate flow, the sending of an alarm signal to a computer, and the addition of ozone to the wastewater of the pipe in an ozone treatment tank downstream of the particle counter. In the tank, the wastewater is treated with 1 g of ozone/m$^3$ of water. After 3 hours the particle count returns to a value below 10000 particles/l. After one more hour, the particle count within the low size range has returned to below 1000 particles/l and the ozone addition is interrupted. During the entire 4 hour time period, in total 20 samples are collected from the permeate flow and stored at a temperature of 5° C., or subjected to microbiological analysis for the presence of coliform organisms, respectively.

Example 3

From a flow of treated wastewater running in a pipe, a flow of 5 l/min is diverted into laser counter operating at a wavelength of from 330 to 870 µm, to continuously count particles over a size interval of from 0.5 to 25 µm. A further flow of water from the pipe is diverted into a ceramic filtering unit wherein it is separated into a permeate flow containing particles capable of passing through filter pores having a diameter of about 5 µm as well as dissolved substances, and a concentrate flow containing particles that have not passed through the pores of the filter.

At time t, the particle count within the large size range of 3 to 25 µm suddenly increases and remains over a preselected threshold value of 1000 particles/l for more than a preselected threshold time of 0.5 minute. This triggers the taking of a 200 ml sample from the concentrate flow, the sending of an alarm signal to a computer, and the addition of ozone to the wastewater of the pipe, in an ozone treatment tank downstream of the particle counter. In the tank, the wastewater is treated with 0.5 g of ozone/m$^3$ of water. After 2 hours the particle count returns to a value below 1000 particles/l. After one more hour, the particle count within the large particle size range has returned to a value of below 500 particles/l and the ozone addition is interrupted.

During the entire 3 hour time period, in total 9 samples are collected from the concentrate flow and stored at a temperature of 5° C. or subjected to microbiological analysis for the presence protozoa, e.g. *Giardia* and *Cryptosporidium*, respectively.

Example 4

In the above EXAMPLES 1 to 3, sensors mounted on the wastewater pipe, upstream of the ozone treatment tank continuously measure dissolved solids, dissolved oxygen, pH, electrical conductivity, temperature and turbidity of the water flowing in the pipe.

Example 5

In the above EXAMPLES 1 to 4, sensors mounted on the wastewater pipe, downstream of the ozone treatment tank continuously measures total dissolved solids, dissolved oxygen, pH, electrical conductivity, temperature and turbidity of the water flowing in the pipe.

Example 6

Treated wastewater was conveyed into an ozone treatment tank as generally illustrated in FIG. 2, wherein ozone was added at a level of 1 g/m$^3$ of water using a mixing chamber as described in WO/2002/017975 (vide supra). The treatment time of the water in the tank was 5 minutes.

The concentration of various drug residues (i.e. residual amounts of pharmaceutical substances) was determined in untreated samples (Control) and in samples of water after the ozone treatment (Treated). The results are listed in Table 1.

TABLE 1

| | | Conc. ng/l | |
|---|---|---|---|
| Substance | Mode of action | Control | Treated |
| Diclofenac | NSAID* | 134 | <0.5 |
| Enalapril | Diuretics | <0.4 | <0.4 |
| Ethinylestradiol | Hormone | <9.1 | <9.1 |
| Furosemide | Diuretics | 251 | <0.2 |
| Sulfamethoxazole | Antibiotics | 30.2 | <0.3 |
| Hydrochlortiazide | Antihypertensive | 375 | <0.6 |
| Ibuprofen | NSAID* | 43.8 | <0.4 |
| Naproxen | NSAID* | 10.2 | <0.9 |
| Estradiol | Hormone | 5.4 | <2.8 |
| Estriol | Hormone | 1.3 | <1.0 |
| Estrone | Hormone | <0.9 | <0.9 |
| Warfarine | Anticoagulant | <0.4 | <0.4 |
| Ramipril | Antihypertensive | <0.1 | <0.1 |
| Norfloxazine | Antibiotics | 12.1 | <0.7 |
| Caffeine | Stimulating | 156 | <0.2 |
| Atenolol | Antihypertensive | 437 | <0.1 |
| Ciprofloxazine | Antibiotics | 26.2 | <1.3 |
| Paracetamol | NSAID* | 21.6 | <0.3 |
| Terbutaline | Asthma medication | 4.0 | <0.1 |
| Trimetoprim | Antibiotics | 50.8 | <0.1 |
| Ranitidine | Ulcer medication | 356 | <0.4 |
| Metoprolol | Antihypertensive | 2064 | <0.1 |
| Oxazepam | Sedative medication | 420 | <0.1 |
| Carbamazepine | Sedative medication | 409 | <0.1 |
| Ketoprofen | NSAID* | 170 | <0.1 |
| Finasteride | Shrinks the prostate | 0.0 | <0.1 |
| Amlodipine | Antihypertensive | 37.7 | <0.1 |
| Propranolol | Antihypertensive | 99.6 | <0.1 |
| Citalopram | Sedative medication | 272 | <0.1 |
| Norethindrone | Hormone | <0.5 | <0.5 |
| Bisoprolol | Antihypertensive | 51.3 | <0.2 |
| Progesterone | Hormone | <0.4 | <0.4 |
| Simvastatin | Lipid-lowering medication | 6.5 | <0.1 |
| Sertralin | Sedative medication | <0.1 | <0.1 |

*NSAID, Nonsteroidal anti-inflammatory drugs.

As shown in EXAMPLE 6, the present invention provides a very efficient method for reducing the amount of drug residues in water, not only in wastewater from chemical and pharmaceutical industry and from households, but also in tap water used for drinking, which is a growing problem globally.

The present invention therefore also provides a method for treatment of water flowing in a pipe, by bringing the water into contact with a low amount of ozone, e.g. 0.1 to 5 mg ozone/m$^3$ of water, for a time period of e.g. 1 minute to 2 hours, e.g. using a mixing chamber such as described in WO/2002/017975 (vide supra). In particular, such a method may be used for reducing residual amounts of chemical substances, such as pharmaceutical compounds and residues thereof, as well as other organic compounds, in treated wastewater and municipal water.

Example 7

Wastewater was treated as described in EXAMPLE 6 and the number of remaining microorganisms, total dissolved carbon and color measured at 410 μm was determined in untreated samples (Control) and in samples of water after the ozone treatment (Ozone treated). The results are listed in Table 2.

TABLE 2

| | Number of microorganisms in sample at temperature | | | Organic carbon | Color at |
|---|---|---|---|---|---|
| Samples | RT | 30° C. | 37° C. | (mg/l) | 410 nm |
| Control | 13*10$^2$ | 16*10$^2$ | 15*10$^2$ | 12.5 | 0.008 |
| Treated 1 | 0 | 0 | 0 | 10 | 0.005 |
| Treated 2 | 0 | 0 | 0 | 10.5 | 0.004 |
| Treated 3 | 0 | 0 | 0 | 10 | 0.005 |

Example 8

From a flow of treated wastewater running in a pipe, a flow of 6 l/min was diverted into laser counter operating at a wavelength of from 330 to 870 μm, to continuously count particles over a size interval of from 1 to 25 μm for a period of several days.

Based on the measured values, reference values $c_{ref}^1=350$ particles/ml for the particle count within a small particle size range of from 1 to 3 μm (Cluster 1) and $c_{ref}^2=100$ particles/ml for the particle count within a large particle size range of from 3 to 25 (Cluster 2) were determined.

Furthermore, threshold values $TV_A^1$ and $TV_A^2$ for taking a sample of water running in the pipe, threshold values $TV_B^1$ and $T_B^2$ for taking a sample of the permeate flow and of the concentrate flow, respectively, threshold $TV_C^1$ and $T_C^2$ for sending an alarm signal, and threshold values $TV_D^1$ and $TV_D^2$ for treating water flowing in the pipe with ozone were selected, together with corresponding threshold times $t_A^1$, $t_A^2$, $t_B^1$, $t_B^2$, $t_C^1$, $t_C^2$, $t_D^1$ and, $t_D^2$.

The selected values are shown in the below Table 3.

TABLE 3

| Threshold Value | Selected value (number of particles/ml) | Threshold time | min |
|---|---|---|---|
| $TV_A^1$ | 400 | $t_A^1$ | 5 |
| $TV_A^2$ | 125 | $t_A^2$ | 5 |
| $TV_B^1$ | 400 | $t_B^1$ | 5 |
| $TV_B^2$ | 125 | $t_B^2$ | 5 |
| $TV_C^1$ | 400 | $t_C^1$ | 5 |
| $TV_C^2$ | 125 | $t_C^2$ | 5 |

TABLE 3-continued

| Threshold Value | Selected value (number of particles/ml) | Threshold time | min |
|---|---|---|---|
| $TV_D^1$ | 400 | $t_D^1$ | 5 |
| $TV_D^2$ | 125 | $t_D^2$ | 5 |

Figure 3:
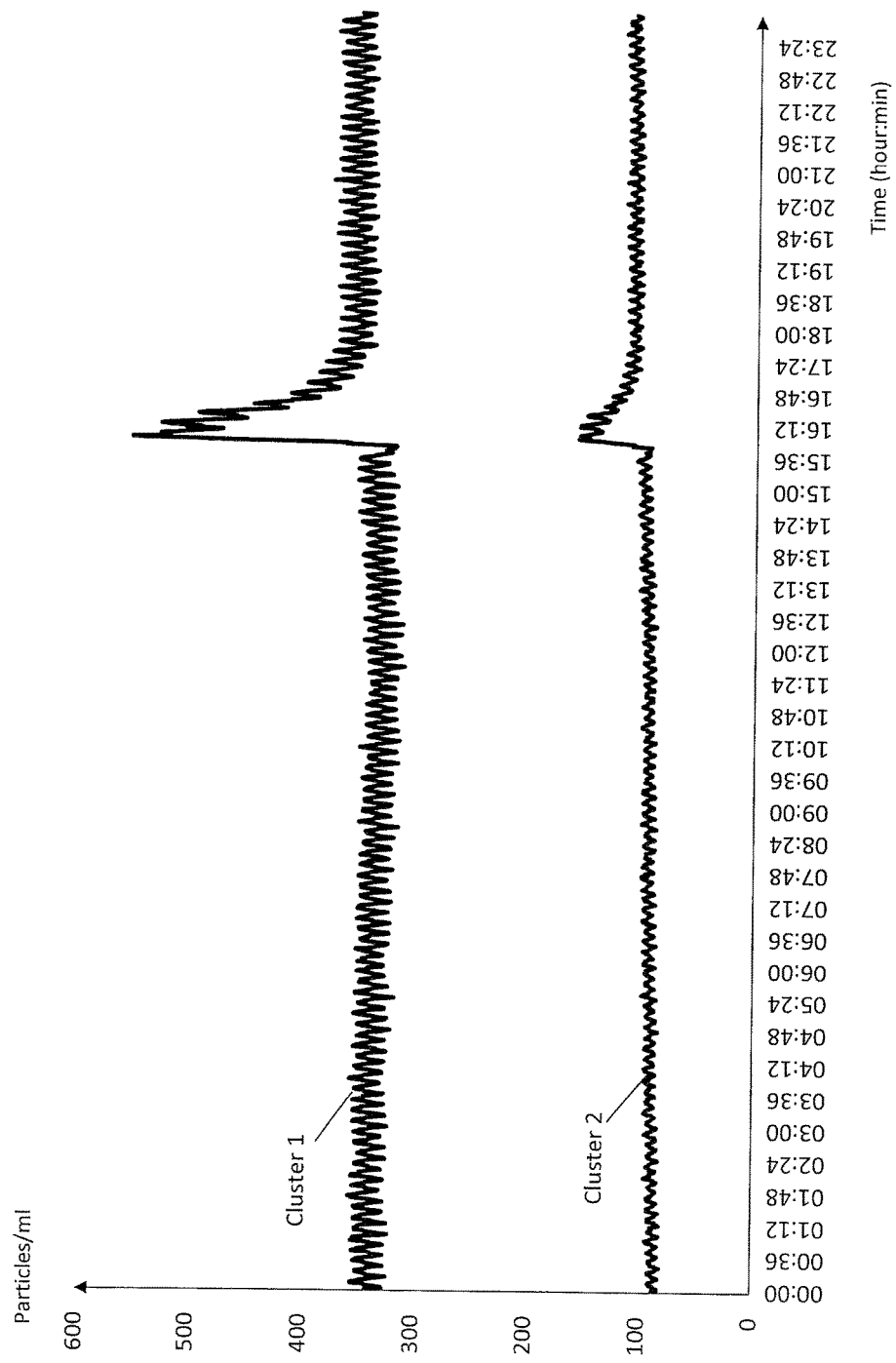
FIG. 3 is a graph showing measured particle count in water during a 24-hour time period. "Cluster 1" corresponds to particles measured within a small particle size range of from 1 to 3 μm and "Cluster 2" corresponds to particles measured within a large particle size range of from 3 to 25 μm.

The water flowing in the pipe was then monitored for a 24 h period of time. In FIG. 3, the number of particles per ml, $c_i^1$ and $c_i^2$, measured at each time $t_i$ within the small size range and within the large size interval respectively, is shown, for the entire period, during which period the threshold values were exceeded once, triggering the sending of an alarm signal, the taking of samples of the permeate and concentrate flow, and addition of ozone.

The invention claimed is:

1. A method for monitoring quality of water flowing in a pipe, the method comprising:
    diverting a flow of water from the pipe into a laser particle counter, the laser particle counter continuously counting particles within a particle size interval $S_n$ in the diverted flow of water so as to continuously determine a number $c_i^n$ of particles within the particle size interval per volume of water;
    comparing $c_i^n$ with a previously determined reference value $c_{ref}^n$ for determining the number of particles per volume of water flowing in the pipe;
    taking a sample of the water from the pipe when $c_i^n$ exceeds a predetermined threshold value $TV_A^n$ for more than a predetermined length of time $t_A^n$;
    diverting a flow of water from the pipe into a filter that separates the flow into a permeate flow and a concentrate flow;
    taking a sample of at least one of the permeate flow and the concentrate flow when $c_i^n$ exceeds a predetermined threshold value $TV_B^n$ for more than a predetermined length of time $t_B^n$; and
    sending an alarm signal when $c_i^n$ exceeds a predetermined threshold value $TV_C^n$ for more than a predetermined length of time $t_C^n$.

2. The method of claim 1, further comprising adding ozone to the water flowing in the pipe when $c_i^n$ exceeds a predetermined threshold value $TV_D^n$ for more than a predetermined length of time $t_D^n$ so as to bring the water flowing in the pipe into contact with ozone for a period of time.

3. The method of claim 2, wherein the water flowing in the pipe is brought into contact with the ozone at a concentration of from 0.05 to 5 mg ozone/$m^3$ of water for a time period of 5 minutes to 2 hours.

4. The method of claim 1, wherein the filter is a ceramic membrane that separates the flow.

5. The method of claim 1, wherein the particle counter continuously counts particles within a particle size interval $S_1$ of from 0.1 to 3 μm to provide a number $c_i^1$ of particles within the size interval per volume of water.

6. The method of claim 5, further comprising taking a sample of the permeate flow of the filtering unit when $c_i^1$ exceeds a predetermined threshold value $TV_B^1$ for more than a predetermined length of time $t_B^1$.

7. The method of claim 6, wherein additionally the particle counter continuously counts particles within a particle size interval $S_2$ of from 3 to 25 μm to provide a number $c_i^2$ of particles within said size interval per volume of water.

8. The method of claim 7, further comprising taking a sample of the concentrate flow of the filtering unit when $c_i^2$ exceeds a predetermined threshold value $TV_B^2$ for more than a predetermined length of time $t_B^2$.

9. The method of claim 8, further comprising performing at least one chemical, biochemical or microbiological analysis of a taken sample of water.

10. The method of claim 1, wherein the laser particle counter continuously counts particles within a particle size interval $S_2$ of from 3 to 25 μm to provide a number $c_i^2$ of particles within said size interval per volume of water.

11. The method of claim 10, further comprising taking a sample of the concentrate flow of the filtering unit when $c_i^2$ exceeds a predetermined threshold value $TV_B^2$ for more than a predetermined length of time $t_B^2$.

12. The method of claim 11, wherein additionally the particle counter continuously counts particles within a particle size interval $S_1$ of from 0.1 to 3 μm to provide a number $c_i^1$ of particles within said size interval per volume of water.

13. The method of claim 1, further comprising performing at least one chemical, biochemical or microbiological analysis of a taken sample of water.

14. The method of claim 1, further comprising:
    continuously measuring at least one physical or chemical parameter of the flow of water;
    comparing a measured value P of the physical or chemical parameter with a reference value Pref of the parameter previously determined for the water; and
    sending an alarm signal when P differs from Pref by more than a predetermined threshold value for more than a predetermined length of time $t_p$.

15. The method of claim 14, wherein the parameter is selected from total dissolved solids, ORP (oxidation reduction potential), dissolved oxygen, pH, electrical conductivity, temperature and turbidity.

16. The method of claim 5, further comprising:
    continuously measuring at least one physical or chemical parameter of the flow of water;
    comparing a measured value P of the physical or chemical parameter with a reference value Pref of the parameter previously determined for the water; and
    sending an alarm signal when P differs from Pref by more than a predetermined threshold value for more than a predetermined length of time $t_p$.

17. The method of claim 1, further comprising:
    continuously measuring at least one physical or chemical parameter of the flow of water;
    comparing a measured value P of the physical or chemical parameter with a reference value Pref of the parameter previously determined for the water; and
    sending an alarm signal when P differs from Pr f by more than a predetermined threshold value for more than a predetermined length of time $t_p$.

* * * * *